US008466324B2

(12) United States Patent
Takeuchi et al.

(10) Patent No.: US 8,466,324 B2
(45) Date of Patent: *Jun. 18, 2013

(54) SULFONE COMPOUND

(75) Inventors: Takeshi Takeuchi, Hyogo (JP); Takehiro Hiyama, Hyogo (JP); Chun Li, Hyogo (JP); Toshihiko Kanki, Hyogo (JP)

(73) Assignee: Sumitomo Seika Chemicals Co., Ltd., Hyogo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/127,892

(22) PCT Filed: Oct. 14, 2009

(86) PCT No.: PCT/JP2009/067792
§ 371 (c)(1),
(2), (4) Date: Jun. 28, 2011

(87) PCT Pub. No.: WO2010/055744
PCT Pub. Date: May 20, 2010

(65) Prior Publication Data
US 2011/0257438 A1 Oct. 20, 2011

(30) Foreign Application Priority Data
Nov. 17, 2008 (JP) ................. 2008-293703

(51) Int. Cl.
*C07C 317/04* (2006.01)

(52) U.S. Cl.
USPC ............................................. 568/28; 568/24

(58) Field of Classification Search
USPC ................................................. 568/28, 24
See application file for complete search history.

(56) References Cited

U.S. PATENT DOCUMENTS

| 4,725,927 | A | 2/1988 | Morimoto et al. | |
| 2011/0306797 | A1* | 12/2011 | Takeuchi et al. | 568/28 |
| 2012/0136175 | A1* | 5/2012 | Fuseya et al. | 568/28 |

FOREIGN PATENT DOCUMENTS

| CN | 1449070 | | 10/2003 |
| CN | 101100450 | | 1/2008 |
| EP | 0 256 486 | | 2/1988 |
| JP | 57-140786 | | 8/1982 |
| JP | 63-239911 | | 5/1988 |
| JP | 64-040457 | | 2/1989 |
| JP | 8-143534 | | 6/1996 |
| JP | 09-147913 | A * | 6/1997 |
| JP | 2000-103779 | | 4/2000 |
| WO | 2006/078866 | | 7/2006 |

OTHER PUBLICATIONS

Xu, K. et al, Journal of the Electrochemical Society, 149 (7) A920-A926 (2002).*
McAllan D.T. et al, Journal of the American Chemical Society, 1951, 73, 3627-32.*
Sato K. et al, Tetrahedron 57 (2001) 2469-2476.*
Chou, et al., "Convenient Desulfonylation Reactions of Cyclic Sulfones with Ultrasonically Dispersed Potassium", Tetrahedron Letters, vol. 26, No. 37, pp. 4495-4498, 1985.
Chou, et al., "Ultrasonically Dispersed Potassium in Organic Synthesis. Water-Acceleration in Reductive C-S Bond Cleavage Reactions", Tetrahedron Letters, vol. 32, No. 29, pp. 3551-3554, 1991.
Hartz, et al., "Design, Synthesis, and biological Evaluation of 1,2,3,7-Tetrahydro-6H-purin-6-one and 3,7-Dihydro-1H-purine-2,6-dione Derivatives as Corticotropin-Releasing Factor$_1$ Receptor Antagonists", J. Med. Chem., vol. 47, No. 19, pp. 4741-4754, 2004.
Cappozzi, et al., "Control of Regioselectivity in the Addition of Sulphenyl Chlorides to 3,3-Dimethylbutyne (t-Butylacetylene) as a Method for Differential Functionalization of Triple Bonds", J. Chem. Soc. Perkin Trans. I, No. 9, pp. 2197-2201, 1982.
Bartlett, et al., "Synthesis of Acetylenes from Carboxylic Acid Derivatives via β-Keto Sulfones", Journal of the American Chemical Society, vol. 100, No. 15, pp. 4852-4858, 1978.
Fawcett, et al., "Carbon-13 NMR Spectra of Monosulphones and Disulphones: Substitution Rules and Conformational Effects", Organic Magnetic Resonance, vol. 10, No. 7, 1978, pp. 360-369.
Stec, et al., "Oxidation of Sulfides with $H_2O_2$ Catalyzed by $Na_2WO_4$ under Phase-Transfer Conditions", Polish J. Chem., vol. 70, No. 9, 1996, pp. 1121-1123.
Rücker, et al., "Unusual Two-Bond $^{13}C$, $^{13}C$ Coupling Constants in Sulphones", Magnetic Resonance in Chemistry, vol. 26, 1988, pp. 1103-1108.
Fuson, et al., "Levinstein Mustard Gas. II. The Addition of 2-Chloro-Ethylsulfenyl Chloride to Propylene", Journal of Organic Chemistry, vol. 11, 1946, pp. 475-481.
Wang, et al., "Oxorhenium(V) Dithiolates Catalyze the Oxidation by tert-Butyl Hydroperoxide of Sulfoxides and Sulfides, Including 4,6-Dimethyldibenzothiophene", Inorg. Chem., vol. 41, 2002, pp. 1272-1280.

* cited by examiner

Primary Examiner — Johann R Richter
Assistant Examiner — Pancham Bakshi
(74) Attorney, Agent, or Firm — Hamre, Schumann, Mueller & Larson, P.C.

(57) ABSTRACT

It is an object of the present invention to provide an aprotic polar solvent mainly useful as a solvent for an electrochemical device, and having a comparatively low melting point and excellent thermal stability.
The present invention is a sulfone compound represented by formula (1),

[Formula 1]

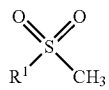

(1)

wherein, in formula (1), $R^1$ represents a C6-C8 branched-chain alkyl group.

2 Claims, No Drawings

SULFONE COMPOUND

TECHNICAL FIELD

The present invention relates to a sulfone compound. More particularly, the present invention relates to a sulfone compound mainly useful for a solvent for an electrochemical device and the like.

BACKGROUND ART

Sulfone compounds are used as extraction solvents or various reaction solvents, and sulfone compounds with a high dielectric constant are also used as solvents for an electrochemical device as aprotic polar solvents. Specifically, proposed use of sulfone compounds as a solvent are seen in devices such as an electric double layer capacitor in which sulfone compounds such as sulfolane and sulfolane derivatives (e.g. 3-methyl sulfolane) are used as an electrolyte (Patent Document 1); and an electric double layer capacitor in which a mixed solvent of propylene carbonate and at least one of sulfolane and a sulfolane derivative such as 3-methyl sulfolane is used as an electrolyte (Patent Document 2)

Aprotic polar solvents used as a solvent for an electrochemical device and the like generally desirably have a low melting point and excellent thermal stability. Depending on types of an electrochemical device, the existence of water within the system can be a problem. In such a case, a solvent with low solubility of water therein is preferably used.

However, sulfone compounds disclosed in Patent Documents 1 and 2 have a relatively high melting point, and therefore have problems such as a decrease in function in a low-temperature environment. Propylene carbonate used together with these sulfone compounds has problems such as inferior thermal stability and relatively high solubility of water in the propylene carbonate.

Patent Document 1: Japanese Kokai Publication Sho-62-237715 (JP-A Sho-62-237715)
Patent Document 2: Japanese Kokai Publication Sho-63-12122 (JP-A Sho-63-12122)

DISCLOSURE OF THE INVENTION

Problems to be Solved by the Invention

It is an object of the present invention to provide an aprotic polar solvent having a comparatively low melting point and excellent thermal stability.

The present invention relates to a sulfone compound represented by the following formula (1).

[Formula 1]

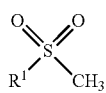

(1)

In formula (1), $R^1$ represents a C6-C8 branched-chain alkyl group.

Examples of the C6-C8 branched-chain alkyl group represented by $R^1$ include methylpentyl group, dimethylbutyl group, ethylbutyl group, methylhexyl group, dimethylpentyl group, ethylpentyl group, trimethylbutyl group, ethylmethylbutyl group, propylbutyl group, methylheptyl group, dimethylhexyl group, ethylhexyl group, trimethylpentyl group, ethylmethylpentyl group, propylpentyl group, tetramethylbutyl group, ethyldimethylbutyl group, diethylbutyl group, propylmethylbutyl group, and the like.

In formula (1), it is not preferable that the branched-chain alkyl group represented by $R^1$ has five carbons or less because the solubility of water therein is too high, and it is not preferable that the branched-chain alkyl group has nine carbons or more because the melting point is too high.

Specific examples of the sulfone compound, represented by formula (1), of the present invention include methyl 2-methylpentyl sulfone, methyl 2,3-dimethylbutyl sulfone, methyl 2-ethylbutyl sulfone, methyl 2-methylhexyl sulfone, methyl 2,3-dimethylpentyl sulfone, methyl 2-ethylpentyl sulfone, methyl 2,2,3-trimethylbutyl sulfone, methyl 2-ethyl-3-methylbutyl sulfone, methyl 2-methylheptyl sulfone, methyl 2,3-dimethylhexyl sulfone, methyl 2-ethylhexyl sulfone, methyl 2-propylpentyl sulfone, methyl 2,2,3-trimethylpentyl sulfone, methyl 2-ethyl-3-methylpentyl sulfone, methyl 2,2,3,3-tetramethylbutyl sulfone, methyl 2-ethyl-2,3-dimethylbutyl sulfone, methyl 2,3-diethylbutyl sulfone, and methyl 2-propyl-3-methylbutyl sulfone, and the like.

Among the sulfone compounds, the C8 branched-chain alkyl group represented by $R^1$ in formula (1) is preferred because of its comparatively low melting point and comparatively low solubility of water therein. Methyl 2-methylheptyl sulfone, methyl 2-propylpentyl sulfone, and methyl 2-ethylhexyl sulfone are more preferred, and methyl 2-ethylhexyl sulfone is still more preferred.

The sulfone compound represented by formula (1) is prepared by, for example, the following steps: a sulfide compound represented by formula (3) is prepared by reacting an organic halide represented by formula (2) and a sodium salt of methanethiol, and the sulfide compound is oxidized using an oxidizing agent.

[Formula 2]

$$R^1\text{—}X \quad (2)$$

In formula (2), $R^1$ represents a C6-C8 branched-chain alkyl group. X represents a halogen atom.

[Formula 3]

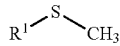

(3)

In formula (3), $R^1$ represents the same group as $R^1$ in formula (2).

The organic halide represented by formula (2) and the sodium salt of methanethiol maybe ones commercially available.

Specific examples of the organic halide include 2-(iodomethyl)heptane, 4-(bromomethyl)heptane, and 3-(chloromethyl)heptane, and the like.

In the reaction of the organic halide represented by formula (2) and the sodium salt of methanethiol, the amount of the sodium salt of methanethiol used is preferably 0.5 to 10 moles, and more preferably 1.0 to 5 moles, relative to 1 mole of the organic halide.

In the reaction of the sodium salt of thiol and the organic halide, a solvent may or may not be used. For example, a solvent may be used when the raw material is solid or the viscosity of the reaction liquid is too high to sufficiently stir. Examples of the solvent are not particularly limited, and examples thereof include alcohols such as methanol, ethanol, propanol, butanol, pentanol, hexanol, heptanol, octanol, nonanol, decanol, undecanol, dodecanol, tridecanol, tetradecanol, cyclohexanol, ethylene glycol, and propylene glycol; ethers such as diethyl ether, dipropyl ether, dibutyl ether, dipentyl ether, dihexyl ether, diheptyl ether, dioctyl ether, tetrahydrofuran, tetrahydropyran, and 1,4-dioxane; nitriles such as acetonitrile, acrylonitrile, and propionitrile; ketones such as acetone, methyl ethyl ketone, methyl isobutyl ketone, and cyclohexanone; esters such as butyrolactone, caprolactone, hexanolactone, and ethyl acetate; sulfoxides such as dimethyl sulfoxide; hydrocarbons such as pentane, hexane, heptane, octane, nonane, decane, undecane, dodecane, cyclohexane, petroleum ether, benzine, kerosene, toluene, xylene, mesitylene, and benzene; and water. Among them, methanol and water are preferably used. Such solvents may be used alone or in combination with one another.

The amount of the solvent is not particularly limited, but is preferably 100 to 5000 parts by weight relative to 100 parts by weight of the organic halide.

The reaction temperature is preferably 0° C. to 200° C., and more preferably 10° C. to 150° C. The reaction time is generally 1 to 30 hours.

In the production method of the sulfone compound of the present invention, specific examples of the oxidizing agent used for the oxidation of the sulfide compound represented by formula (3) are not particularly limited, and thereof include potassium permanganate, chromic acid, oxygen, hydrogen peroxide water, and organic peroxides such as 3-chloroperbenzoic acid. Particularly, hydrogen peroxide water is preferably used.

The amount of the oxidizing agent used is preferably 1.8 to 10 moles, and more preferably 2 to 5 moles, relative to 1 mole of the sulfide compound.

In the oxidation of the sulfide compound, a solvent may or may not be used. For example, a solvent may be used when the raw material is solid or the viscosity of reaction liquid is too high to sufficiently stir. Examples of the solvent are not particularly limited, and thereof include alkyl halides such as carbon tetrachloride, chloroform, dichloromethane, bromopropane, bromobutane, bromopentane, bromohexane, methyl iodide, ethyl iodide, and propyl iodide; ketones such as acetone, methyl ethyl ketone, methyl isobutyl ketone, and cyclohexanone; hydrocarbons such as pentane, hexane, heptane, octane, nonane, decane, undecane, dodecane, cyclohexane, petroleum ether, benzine, kerosene, toluene, xylene, mesitylene, and benzene; and water. Among them, alkyl halides and water are preferably used. Such solvents may be used alone, or two or more thereof may be used in combination.

The amount of the solvent is not particularly limited, but is preferably 100 to 5000 parts by weight relative to 100 parts by weight of the sulfide compound.

The reaction temperature is preferably 0° C. to 200° C., and more preferably 10° C. to 150° C. The reaction time is generally 1 to 30 hours.

The sulfone compound thus obtained is rinsed and separated, if needed, and can be isolated by distillation.

The sulfone compound of the present invention can be suitably used, for example, as a solvent for an electrochemical device, such as an electrolyte solvent.

Examples of the electrochemical device include lithium primary batteries, lithium secondary batteries, lithium ion batteries, fuel cells, solar cells, electric double layer capacitors, and the like.

The sulfone compound of the present invention has a low solubility of water therein. Therefore, when the sulfone compound is used as the solvent for an electrochemical device, mixing with water is suppressed, which prevents occurrence of a decrease in current efficiency, an increase in internal pressure, and the like. The sulfone compound of the present invention also has a comparatively low melting point and excellent thermal stability, and can be therefore safe to be used at a wide temperature range from low tempertures to high temperatures. Further, the sulfone compound of the present invention has low viscosity, and therefore ion conductivity of an electrolyte can be significantly increased to achieve high electrical properties.

Effects of the Invention

The sulfone compound of the present invention is an aprotic polar solvent having a comparatively low melting point, excellent thermal stability, and a low solubility of water therein. Accordingly, the sulfone compound is useful mainly as a solvent for an electrochemical device.

MODE(S) FOR CARRYING OUT THE INVENTION

Hereinafter, the present invention will be described in further detail referring to the following examples. The present invention is not limited to these examples.

EXAMPLE 1

Synthesis of methyl 2-ethylhexyl sulfone (MEHS)

A 500-mL four-necked flask equipped with a stirrer, a thermometer, and a condenser was charged with 74.4 g (0.50 mol) of 3-(chloromethyl)heptane under nitrogen atmosphere. An amount of 187.8 g (0.75 mol) of a 28% methyl mercaptan sodium aqueous solution was gradually added the flask, and the mixture was then stirred for two hours while maintaining the temperature thereof at 60° C. To the mixture was added 50 ml of dichloromethane, and the mixture was stirred for 10 minutes. The dichloromethane layer was then isolated and rinsed once with 30 mL of ultrapure water. To the resulting dichloromethane layer was added 102.0 g (1.05 mol) of a 35% hydrogen peroxide solution. The solution was then stirred at 60° C. for two hours, and the dichloromethane layer was distilled to give 86.5 g of methyl 2-ethylhexyl sulfone in a colorless, transparent liquid form. The yield of the obtained methyl 2-ethylhexyl sulfone was 90% relative to 3-(chloromethyl)heptane.

The melting point and the exothermic onset temperature of the obtained methyl 2-ethylhexyl sulfone were measured using a differential scanning calorimeter under nitrogen atmosphere. In addition, solubility of water in the 2-ethylhexyl sulfone was determined by measurement of water content of the sulfone compound saturated with dissolved water using a Karl Fischer coulometric titrator.

The obtained methyl 2-ethylhexyl sulfone was identified because it had the physical properties described below.

$^1$-H-NMR (400 MHz, solvent: $CDCl_3$): 0.92 (m, 6H), 1.30 (m, 3H), 1.52 (m, 4H), 2.06 (m, 2H), 2.91 (S, 3H) and 2.95 (d, J=5.9 Hz, 2H)

Elemental analysis: C, 56.2; H, 10.5; and S, 16.7 (calculated value: C, 56.2; H, 10.2; and S, 16.7)

Table 1 shows the results of the measurement of the melting point, exothermic onset temperature, and solubility of water in a compound, of the compound of Example 1 and of compounds for comparison, namely propylene carbonate as Comparative Example 1 and sulfolane as Comparative Example 2.

TABLE 1

| Compound | Melting point (° C.) | Exothermic onset temperature (° C.) | Solubility of water (25° C.) (g/100 g) |
|---|---|---|---|
| Example 1 | MEHS | 10 | 167 | 3.0 |
| Comparative Example 1 | Propylene carbonate | −49 | 73 | 8.4 |
| Comparative Example 2 | Sulfolane | 29 | 210 | Freely mixed |

Industrial Applicability

According to the present invention, an aprotic polar solvent that is useful mainly as a solvent for an electrochemical device, and has a comparatively low melting point and excellent thermal stability can be provided.

The invention claimed is:

1. A sulfone compound represented by following formula (1),

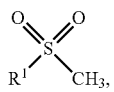

(1)

wherein, in formula (1), $R^1$ represents a $C_6$-$C_8$ branched-chain alkyl group selected from the group consisting of a dimethylbutyl group, an ethylbutyl group, a dimethylpentyl group, an ethylpentyl group, a trimethylbutyl group, an ethylmethylbutyl group, a propylbutyl group, a methylheptyl group, a dimethylhexyl group, an ethylhexyl group, an ethylmethylpentyl group, a proylpentyl group, a tetramethylbutyl group, an ethyldimethylbutyl group a diethylbutyl group, and a propylmethylbutyl group.

2. The sulfone compound according to claim 1, wherein, in the formula (1), $R^1$ is a 2-ethylhexyl group.

* * * * *